United States Patent
Zierhofer (10) Patent No.: US 6,600,955 B1
(45) Date of Patent: Jul. 29, 2003

(54) MULTICHANNEL COCHLEAR IMPLANT WITH NEURAL RESPONSE TELEMETRY

(75) Inventor: Clemens M. Zierhofer, Kundl (AT)

(73) Assignee: Med-El Elektromedizinishe Geraete GmbH, Innsbruck (AT)

( * ) Notice: Subject to any disclaimer, the term of this patent is extended or adjusted under 35 U.S.C. 154(b) by 17 days.

(21) Appl. No.: 09/621,444

(22) Filed: Jul. 21, 2000

Related U.S. Application Data (60) Provisional application No. 60/144,799, filed on Jul. 21, 1999.

(51) Int. Cl.[7] .................................................. A61N 1/36
(52) U.S. Cl. ........................................... 607/57; 607/74
(58) Field of Search ................................ 128/897–898; 600/379; 607/1–2, 4–5, 55–57, 66, 74–76, 137, 9, 15, 68, 70, 72; 623/10

(56) References Cited

U.S. PATENT DOCUMENTS

| | | | |
|---|---|---|---|
| 4,284,856 A | | 8/1981 | Hochmair et al. ...... 179/107 E |
| 4,428,377 A | | 1/1984 | Zollner et al. ........... 128/419 R |
| 4,532,930 A | * | 8/1985 | Crosby et al. ................. 607/57 |
| 4,592,359 A | * | 6/1986 | Galbraith ..................... 607/57 |
| 5,549,658 A | | 8/1996 | Shannon et al. ............... 607/57 |
| 5,601,617 A | * | 2/1997 | Loeb et al. .................... 607/56 |
| 5,609,616 A | | 3/1997 | Schulman et al. ............ 607/56 |
| 5,649,970 A | * | 7/1997 | Loeb et al. .................... 607/57 |
| 5,741,314 A | | 4/1998 | Daly et al. ..................... 607/60 |
| 5,749,912 A | | 5/1998 | Zhang et al. .................. 607/57 |
| 5,824,022 A | | 10/1998 | Zilberman et al. ............ 607/57 |
| 5,938,691 A | | 8/1999 | Schulman et al. ............ 607/57 |
| 6,181,969 B1 | * | 1/2001 | Gord ........................... 607/57 |

FOREIGN PATENT DOCUMENTS

| | | | |
|---|---|---|---|
| WO | WO 94/14376 | 7/1994 | |
| WO | WO 97/48447 | 12/1997 | |
| WO | WO 99/35882 | 7/1999 | ........ H04R/25/00 |

OTHER PUBLICATIONS

Zierhofer et al., Electronic Design of a Cochlear Implant for Multichannel High–Rate Pulsatile Stimulation Strategies, Mar. 1995, Transactions of Rehabilitation Engineering vol. 3, No. 1.*

Rattay F. "Analysis of models for external stimulation of axons", IEEE–Trans. Biomed. Eng., vol. BME–33, No. 10, pp. 974–977, Oct. 1986.

Ragheb T. et al. "Electrical properties of metallic electrodes" Med. & Biol. Eng.& Comput., vol. 28, No. 2, pp. 182–186, Mar. 1990.

Wilson B. S. et al. "Better speech recognition with cochlear implants", Nature, vol. 352, pp. 236–238, Jul. 18, 1991.

Mayer S. et al. "Faradic resistance of the electrode/electrolyte interface", Med. & Biol. Eng.& Comput., vol. 30, No. 5, pp. 538–542, Sep. 1992.

(List continued on next page.)

*Primary Examiner*—Kennedy Schaetzle
*Assistant Examiner*—Kristen Droesch
(74) *Attorney, Agent, or Firm*—Bromberg & Sunstein LLP (57) ABSTRACT

A circuit for generating a sign-correlated simultaneous pulsatile stimulation. The circuit includes a plurality of circuit paths coupled in parallel between a voltage rail and ground. Each circuit path includes an electrode coupled to the voltage rail via a first current source and to the ground via a second current source, the first current source and the second current source having opposite sign. A remote ground electrode is coupled to the voltage rail via a first switch and to the ground via a second switch. The stimulation is achieved by activating all current sources of the same sign and switching the remote ground electrode to create current in the remote ground electrode equal to the sum of all single electrode currents.

8 Claims, 7 Drawing Sheets

OTHER PUBLICATIONS

Thao N.T. "Deterministic analysis of oversampled A/D conversion and decoding improvement based on consistent estimates", IEEE–Trans. Signal Proc., vol. 42, No. 3, pp. 519–531, Mar. 1994.

Frijns J. "A model of myelinated nerve fibres for electrical prosthesis design", Med. & Biol. Eng. & Comput., vol. 32, No. 3, pp. 391–398, May 1994.

Gantz B. et al. "Inoperative measures of electrically evoked auditory nerve compound action potentials", American Journal of Otology, vol. 15, No. 2, pp. 137–144, Mar. 1994.

Zierhofer C. et al. "Electronic design of a cochlear implant for multichannel high–rate pulsatile stimulation strategies", IEEE Trans. Rehab. Eng., vol. 3, No. 1, pp. 112–116, Mar. 1995.

Brown C. J. et al. "Electrically evoled whole nerve action potentials in ineraid cochlear implant users: responses to different stimulating electrode configurations and comparison to psychophysical responses", Journal of Speech and Hearing Research, vol. 39, pp. 453–467, Jun. 1996.

Zierhofer C.M. "Adaptive Sigma–Delta Modulation with one bit quantization", IEEE–Trans. CAS II, vol. 47, No. 5, pp. 408–415, May 2000.

Wilson B. S. et al. "Better speech recognition with cochlear implants" Nature 352:236-238 Jul. 1991.

Wilson B. S. et al. "Speech processors for auditory prostheses" Seventh Quarterly Progress Report Feb. 1 through Apr. 30, 1994 NIH Contact N01–DC–2–2401.

Kral A. et al. "Spatial resolution of cochlear implants: the electrical field and excitation of auditory afferents" Hearing Research 121:11–28 1998.

Matsuoka A. J. "Compound action potentials evoked by electrical pulse trains: effects of stimulus parameters on response patterns" Thesis at University of Iowa Jul. 1998.

PCT/ISA/210 International Search Report International application No. PCT/IB00/01338 International filing date Aug. 25, 2000.

* cited by examiner

MULTICHANNEL COCHLEAR IMPLANT WITH NEURAL RESPONSE TELEMETRY

PRIORITY

This application cliams priority from U.S. provisional patent application Ser. No. 60/144,799, filed Jul. 21, 1999, entitled Multi-channel Cochlear Implant with Neural Response Telemetry, the disclosure of which is incorporated herein by reference.

FIELD OF THE INVENTION

The present invention relates to bit format systems for functional electrical stimulation, and more particularly, to systems for electrostimulation of the acoustic nerve.

BACKGROUND

Cochlear implants (inner ear prostheses) are a means to help profoundly deaf or severely hearing impaired persons. Unlike conventional hearing aids, which just apply an amplified and modified sound signal, a cochlear implant is based on direct electrical stimulation of the acoustic nerve. The intention of a cochlear implant is to stimulate nervous structures in the inner ear electrically in such a way that hearing impressions most similar to normal hearing are obtained.

A cochlear prosthesis essentially consists of two parts, the speech processor and the implanted stimulator. The speech processor contains the power supply (batteries) of the overall system and is used to perform signal processing of the acoustic signal to extract the stimulation parameters. The stimulator (implant) generates the stimulation patterns and conducts them to the nervous tissue by means of an electrode array which usually is positioned in the scala tympani in the inner ear. The connection between the speech processor and the implanted receiver can be established by means of encoding digital information in an rf-channel involving an inductively coupled coils system.

Figure 1:
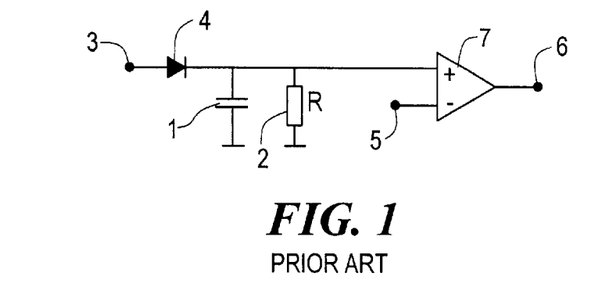
FIG. 1 schematically shows a standard envelope detection circuit (prior art)

Decoding the information within the implant can require envelope detection. Envelope detection of an RF signal within an implant is usually performed with a simple circuit, as shown in FIG. 1, composed of a rectifier diode 4, an RC-network 1 and 2, and a comparator 7. A drawback to this circuit is that the total power consumption of the RC-network, due in part to the ohmic resistor, can be considerable when taking into account the cochlear implant application.

Stimulation strategies employing high-rate pulsatile stimuli in multichannel electrode arrays have proved to be successful in giving very high levels of speech recognition. One example therefore is the so-called "Continuous Interleaved Sampling (CIS)"-strategy, as described by Wilson B. S., Finley C. C., Lawson D. T., Wolford R. D., Eddington D. K., Rabinowitz W. M., "Better speech recognition with cochlear implants," Nature, vol. 352:236–238 (1991), which is incorporated herein by reference. For CIS, symmetrical biphasic current pulses are used, which are strictly non-overlapping in time. The rate per channel typically is higher than 800 pulses/sec.

Stimulation strategies based on simultaneous activation of electrode currents so far have not shown any advantage as compared to CIS. The basic problem is the spatial channel interaction caused by conductive tissue in the scala tympani between the stimulation electrodes. If two or more stimulation current sources are activated simultaneously, and if there is no correlation between them, the currents will flow between the active electrodes and do not reach the regions of neurons which are intended to be stimulated. The problem might get less severe with new stimulation electrode designs, where the electrodes are much closer to the modiolus as compared to existing electrodes, as described by Kuzma J., "Evaluation of new modiolus-hugging electrode concepts in a transparent model of the cochlea," proc. 4th European Symp. on Pediatric Cochlear Implantation, 's-Hertogenbosch, The Netherlands (June 1998), which is incorporated herein by reference.

For high-rate pulsatile stimulation strategies, some patient specific parameters have to be determined. This is done some weeks after surgery in a so called "fitting"-procedure. For given phase duration of stimulation pulses and for given stimulation rate, two key parameters have to be determined for each stimulation channel:

1. the minimum amplitude of biphasic current pulses necessary to elicit a hearing sensation (Threshold Level, or THL); and
2. the amplitude resulting in a hearing sensation at a comfortable level (Most Comfort Level, or MCL).

For stimulation, only amplitudes between MCL and THL (for each channel) are used. The dynamic range between MCL and THL typically is between 6–12 dB. However, the absolute positions of MCLs and THLs vary considerably between patients, and differences can reach up to 40 dB. To cover these absolute variations, the overall dynamic range for stimulation in currently used implants typically is about 60 dB.

At the moment, MCLs and THLs are estimated during the fitting procedure by applying stimulation pulses and asking the patient about his/her subjective impression. This method usually works without problems with postlingually deaf patients. However, problems occur with prelingually or congenitally deaf patients, and in this group all ages—from small children to adults—are concerned. These patients are usually neither able to interpret nor to describe hearing impressions, and only rough estimations of MCLs and THLs based on behavioral methods are possible. Especially the situation of congenitally deaf small children needs to be mentioned here. An adequate acoustic input is extremely important for the infant's speech and hearing development, and this input in many cases can be provided with a properly fitted cochlear implant.

One approach for an objective measurement of MCLs and THLs is based on the measurement of the EAPs (Electrically evoked Action Potentials), as described by Gantz B., Brown C. J., Abbas P. J., "Intraoperative Measures of Electrically Evoked Auditory Nerve Compound Action Potentials," American Journal of Otology 15 (2):137–144 (1994), which is incorporated herein by reference. In this approach, the overall response of the acoustic nerve to an electrical stimulus is measured very close to the position of nerve excitation. This neural response is caused by the superposition of single neural responses at the outside of the axon membranes. The amplitude of the EAP at the measurement position is between 10 $\mu V$ and 1000 $\mu V$. Information about MCL and THL at a particular electrode position can first of all be expected from the so called "amplitude growth function," as described by Brown C. J., Abbas P. J., Borland J., Bertschy M. R., "Electrically evoked whole nerve action potentials in Ineraid cochlear implant users: responses to different stimulating electrode configurations and comparison to psychophysical responses," Journal of Speech and Hearing Research, vol. 39:453–467 (June 1996), which is incorporated herein by reference. This function is the relation between the amplitude of the stimulation pulse and the peak-to-peak voltage of the EAP. Another interesting relation is the so called "recovery function". Here, stimulation is achieved with two pulses with varying interpulse-interval. The recovery function as the relation of the amplitude of the 2nd EAP and the interpulse-interval allows one to draw conclusions about the refractory properties and particular properties concerning the time resolution of the acoustic nerve.

SUMMARY OF THE INVENTION

In accordance with one aspect of the invention, a data transmission system having a coding unit coupled to a communications channel, that transmits encoded digital information having defined minimum and maximum durations of logical states "low" and "high". A decoding unit is coupled to the communication channel, which receives and decodes the information. The decoder is comprised of a free running local oscillator LO coupled to an array of sampling capacitors, that effectively sample the information using the LO frequency. A circuit is coupled to the sampling capacitors, that decodes the information and corrects any mismatch between nominal and actual LO frequency. In another related embodiment, the encoded digitial information is contained in an RF signal. The data transmission system can be used in a cochlear implant system or an implantable system for functional electrostimulation.

In accordance with another embodiment of the invention, a data decoder system coupled to a communication channel that decodes information received. The decoder has a free running local oscillator LO coupled to an array of sampling capacitors, that effectively sample the information using the LO frequency. A circuit is coupled to the sampling capacitors, that decodes the information and corrects any mismatch between the nominal and actual LO frequency. The encoded digital information can be contained in an RF signal. The data decoder system can be used in a cochlear implant system, or a implantable system for functional electrostimulation.

In accordance with another emodiment of the invention, A circuit for detecting the envelope of an input signal, the circuit comprising a first sampling capacitor C1 and a second sampling capacitor C2, both capacitors coupled to ground. A first switching matrix S1 cyclically couples C1 to an input signal via a rectifier diode, the input signal being encoded with digital data; a first input of a comparator; and ground. A second switch matrix S2 cyclically couples C2 to the input signal via the rectifier diode; the first input of the comparator, and ground. A local oscillator is coupled to S1 and S2, that controls switch matrices S1 and S2, the local oscillator having period T. A dc-reference is coupled to a second input of the comparator. A flip flop is coupled to the comparator output, the flip flop being clocked by the local oscillator producing a data bit stream output indicative of the input signal's envelope the circuit may be used for detecting the envelope of an input signal in a cochlear implant, wherein the input signal is an RF signal encoded with digital information. In a related emodiment, a first logical state is encoded in the input signal by the sequence "RF-carrier off" followed by "RF-carrier on," and a second logical zero is encoded by the sequence "RF-carrier on" followed by "RF-carrier off." The RF input signal may be encoded using Amplitude Shift Keying Modulation, the digital data employing a self-clocking bit format. In another related embodiment, C1 and C2 are sequentially and cyclically coupled via the switching matrices to the input signal via the rectifier diode for time duration T/2 (phase D), the comparator for time duration T (phase C), and ground for time duration T/2 (phase G). S2's switching sequence is offset from S1's switching sequence by a phase shift of T. The clock of the flip flop may be activated at the end of phases C on the negative slope of the local oscillator.

In accordance with another aspect of the invention, a method for data telemetry, where digital data is encoded into an input signal. The input signal is applied via a rectifier diode to a first switch matrix S1 and a second switch matrix S2, with S1 being coupled to a first sampling capacitor C1 and S2 being coupled to a second sampling capacitor C2. A local oscillator signal with period T is applied that controls S1 and S2, so as to cyclically couple C1 and C2 to the RF signal, a first input to a comparator, and ground. The comparator compares the first input to a DC reference voltage. The output of the comparator is then sampled via a flip flop clocked by the local oscillator, with the flip flop outputting a data bit stream representative of the envelope of the input signal having encoded information.

In another related embodiment, the data telemetry method detects the envelope of an input signal in a cochlear implant, the input signal is an RF encoded signal encoded with digital data. A first logical state may be encoded in the input signal by the sequence "RF-carrier off" followed by "RF-carrier on," and a second logical state is encoded by the sequence "RF-carrier on" followed by "RF-carrier off." The input signal can contain special bit formats, such that the signal can be switched on or off for longer durations, such as 3B/2, B being the bit duration. In another related embodiment, the RF signal is encoded using Amplitude Shift Keying Modulation, the digital data employing a self-clocking bit format. In another embodiment, the sampling capacitors C1 and C2 are sequentially and cyclically coupled via the switching matrices to the input signal for time duration T/2 (phase D), the 1st input of the comparator for time duration T (phase C), and to ground for time duration T/2 (phase G), with S2's switching sequence being offset from S1's switching sequence by a phase shift of T. In another embodiment, the clock of the flip flop is activated at the end of phases C on the negative slope of the local oscillator.

In another related embodiment, the data bit stream is decoded, including distinguishing four different data bit stream states, a "short low" L1 defined by a data bit stream pattern of 0 or 00, a "short high" H1 defined by a data bit stream pattern of 11 or 111, a "long low" L2 defined by a data bit stream pattern of 000 or 000, and a "long high" H2 defined by a data bit stream pattern of 1111 or 11111. Two additional bit states may be distinguished, an "extra long low" L3 defined by a data bit stream pattern of 00000 or 000000, and an "extra long high" H3 defined by a data bit stream pattern of 111111 or 1111111. Triplet sequences may also be distinguishable, a triplet sequence having a starting short state L1 or H1, followed by a sequence of strictly alternating states L3 or H3, and a terminating short state L1 or H1. The triplet sequence can be used for control and synchronization. In another related embodiment, data telemetry is achieved by data word formats having a starting triplet sequence, followed by a particular number of information bits with self-clocking format; and a terminating triplet sequence. These data word formats can allow allow high rate stimulation strategies based on sign-correlated, simultaneous stimulation pulses. In another related embodiment, the encoded information allows stimulation with sign-correlated biphasic, symmetrical pulses, stimulation with sign-correlated triphasic, symmetrical pulses, and stimulation with sign-correlated triphasic pulses. In another embodiment of the invention, a method of employing high-rate pulsatile stimulation receives encoded information, decodes the information, and applies stimulation modes based on the decoded information. The stimulaton modes comprising sign-correlated biphasic, symmetrical pulses, sign-correlated triphasic, symmetrical pulses, and sign-correlated triphasic pulses.

In accordance with another aspect of the invention, a circuit and method for generating sign-correlated simultaneous pulsatile stimuli in a cochlear implant simultaneously applying current of same sign to a plurality of electrodes Ei. A remote ground is switched to either Vdd or ground, creating a current in the remote ground electrode equal to the sum of all single electrode Ei currents. In a related embodiment, each electrode is coupled via a switch to either a first or second current source, the second current source having the opposite sign as the first current source. In a related embodiment, the acoustic nerve is stimulated by the sign-correlated simultaneous pulsatile stimuli. The sign-correlated simultaneous pulsatile stimuli may be generated in a cochlear implant. Pulses generated can include sign-correlated biphasic, symmetrical pulses, sign-correlated triphasic, symmetrical pulses, and sign-correlated triphasic pulses.

In another embodiment, a circuit and method for measuring electrically evoked action potentials samples an input signal across a measurement electrode and a reference electrode, the measurement electrode and reference electrode being coupled in parallel. The sampled signal is then amplified and converted into a high frequency one bit sigma-delta sequence, the sequence being stored in the implant's memory. In a related embodiment, the input signal is sampled with a first double switch. In a further related embodiment, the amplifier is a differential amplifier. The measurement electrode and the reference electrode may be coupled to the differential amplifier via coupling capacitors. In another related embodiment, the amplified analog signal is sampled and held before being digitized. In another related embodiment, the sigma-delta data sequence is transferred from memory to outside by load modulation, allowing reconstruction of the electrically evoked action potential signal from the digitized data to be achieved off-line. The method can be used in a cochlear implant.

In another embodiment of the invention, a circuit and method for measuring stimulus artifacts samples an input an input voltage across a measurement electrode and a reference electrode with a sampling capacitor to create a sampled input. At a programmable time instant, the sampled input is output to a sigma-delta modulator via a switch, to produce a sigma-delta data sequence. The sigma-delta data sequence is then sent to memory. In a related embodiment, the sigma-delta data sequence is sent from memory to outside by load modulation, allowing reconstruction of the electrically evoked action potential signal from the digitized data to be achieved off-line.

BRIEF DESCRIPTION OF THE DRAWINGS

The foregoing features of the invention will be more readily understood by reference to the following detailed description, taken with reference to the accompanying drawings, in which:

FIG. 5 shows examples for correct bit-synchronization for fixed LO-rate $f_{LO}$, and different bit rates $f_{BIT}$    a. $f_{BIT}=f_{LO}/4.0$    b. $f_{BIT}\approx f_{LO}/3.6$    c. $f_{BIT}\approx f_{LO}/4.4$ FIG. 7 shows examples of sign-correlated simultaneous stimuli in different channels Note: all simultaneous pulses are 100% overlapping in time, and the signs of all simultaneous stimulation currents are equal    a. biphasic symmetrical    b. triphasic symmetrical    c. triphasic-precision FIG. 8 schematically shows a circuit for generation of pulses for non-simultaneous stimulation strategies (prior art)

DETAILED DESCRIPTION OF THE INVENTION

A cochlear implant is described which is designed to implement high rate simultaneous or non-simultaneous stimulation strategies. In the case of simultaneous stimulation, sign-correlated pulsatile stimuli are employed. Sign-correlated means that the pulses are 100% overlapping in time and that for each phase, the signs of current flow are identical. Charge balanced biphasic and triphasic pulses can be applied.

The high data transfer rate necessary to convey sufficient stimulation information for simultaneous strategies is based on a novel data decoding concept. Data decoding is achieved by sampling of the rf-signal by means of two sampling capacitors and subsequent digital data processing. A free running local oscillator (LO) is used, where the clock frequency is about four times higher than the bit rate. The mismatch between the actual and nominal LO-clock frequency is digitally corrected.

The implant is equipped with an EAP measurement system. For EAP measurement, one of the intra-cochlear electrodes is addressed as sensing electrode. The sensing electrode can also be positioned outside the cochlear to measure other bio-sginals. The measurement system basically consists of an instrumentation amplifier and a subsequent sigma-delta modulator. During measurement, the EAP-signal is amplified and converted to a high-frequency one-bit sigma-delta sequence. This sequence is stored to a memory in the implant. Random Access Memory (RAM) may be utilized. After measurement, these data are sent to outside by means of load modulation, and the EAP-signal reconstruction from the sigma-delta rough data can be achieved off-line.

Self-clocking Bit Format with Amplitude Shift Keying

One possibility for encoding digital data in an rf-channel is to use Amplitude Shift Keying (ASK). For ASK, the rf-carrier is switched on and off controlled by the digital information sequence. Thus the information is contained in the envelope of the rf-signal, and decoding within the implant requires envelope detection.

Figure 2:
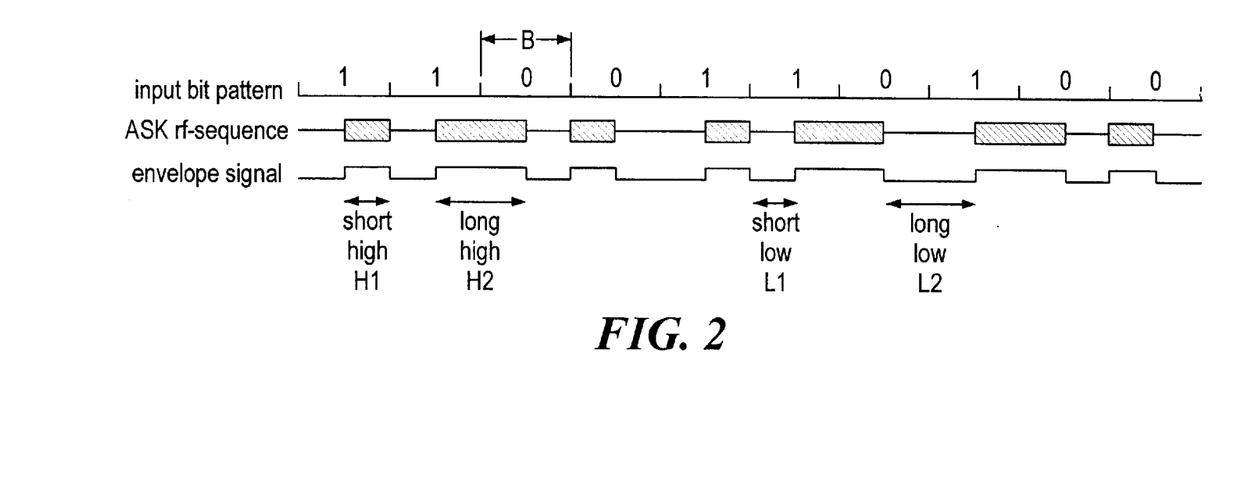
FIG. 2 shows a bit sequence with a self-clocking bit format

If the bandwidth of the rf-channel is sufficiently high, a self-clocking bit format can be defined. For example, a logical "one" is encoded into the sequence "rf-carrier off"

followed by "rf-carrier on," a logical "zero" is encoded into the reverse sequence. Assuming a duty ratio of 50%, the mean energy flow then is independent of the data content transmitted, since the time the rf-carrier is switched on is equal to the time it is switched off. An example of a bit sequence employing the self-clocking bit format is depicted in FIG. 2. The first trace shows the bit pattern, the second the associated rf-sequence in self-clocking bit format, where the black squares represent "rf-on"-states. Regarding the associated envelope signal in trace 3, four different states "short low, "short high," "long low," and "long high," occur. For convenience, these states are abbreviated by L1, H1, L2, and H2, where the letter ("L" or "H") characterizes the state "low" or "high," and the subsequent number defines the duration of the state in multiples of B/2 (bit duration B). States L1 and H1 appear in sequences of continuing logical "zeros" or "ones," states L2 and H2 occur, if logical "zeros" and "ones" alternate.

Novel Approach for Envelope Detection: Envelope Sampling

As stated above, envelope detection of an RF input signal 3 within an implant is usually performed with a simple circuit, as shown in FIG. 1, composed of a rectifier diode 4, an RC-network 1 and 2, and a comparator 7. In the "rf-on"-state of the ASK-signal, the voltage across the RC-network 1 and 2 is approximately equal to the amplitude of the RF input signal 3. During the "rf-off"-state, the capacitor 1 is discharged across the resistor 2. Ideally, the voltage across the capacitor 1 tracks the envelope of the RF input signal 3. To obtain steep edges of the output signal 6 a comparator 7 is involved. The two comparator input signals are the voltage across the capacitor 1, and a reference dc-voltage 5 which is typically equal to about 50% of the rf-amplitude. In the standard approach, the comparator output signal 6 is used for further signal processing.

The signal transition which necessarily occurs in the middle of each bit (cf. FIG. 1) can be exploited for clock generation within the implant. For bit decoding a non-retriggerable mono-flop is used, which is triggered by both the positive and the negative slope of the envelope signal, when it is in its waiting position, as described by Zierhofer C., Hochmair I., Hochmair E., "Electronic design of a cochlear implant for multichannel high-rate pulsatile stimulation strategies," IEEE Trans. Rehab. Eng., vol.3:112–116 (March 1995), which is incorporated herein by reference.

Regarding the power consumption of the RC-network, it is clear that for a given time constant τ=RC, resistor 2 and capacitor 1 have to be as large and as small as possible, respectively. However, for reliable operation, capacitor 1 cannot be arbitrarily small. Assuming a typical lower limit C=10 pF, and a time constant of τ=0.1 μs results in a resistor=10 kΩ. If an rf-amplitude of U=5V is supposed, the current through the resistor 2 in the "rf-on"-state is 500 μA, resulting in a power consumption of 2.5 mW. For a self clocking bit format, the mean power consumption is $P_R$=1.25 mW. Another contribution to the power consumption stems from charging/discharging of capacitor 1. Assuming C=10 pF, a maximum voltage of 5V, a bit rate of $f_{bit}$=600 kbit/s, and supposing that the capacitor 1 is charged/discharged once in a bit period, the resulting power is $P_{charge}$= 0.075 mW. So the total power consumption of the RC-network is about $P_{tot}=P_R+P_{charge}$=1.325 mW, which is considerable in a cochlear implant application. Note that for the given parameters, $P_{charge}$ is much smaller than $P_R$.

Figure 3:
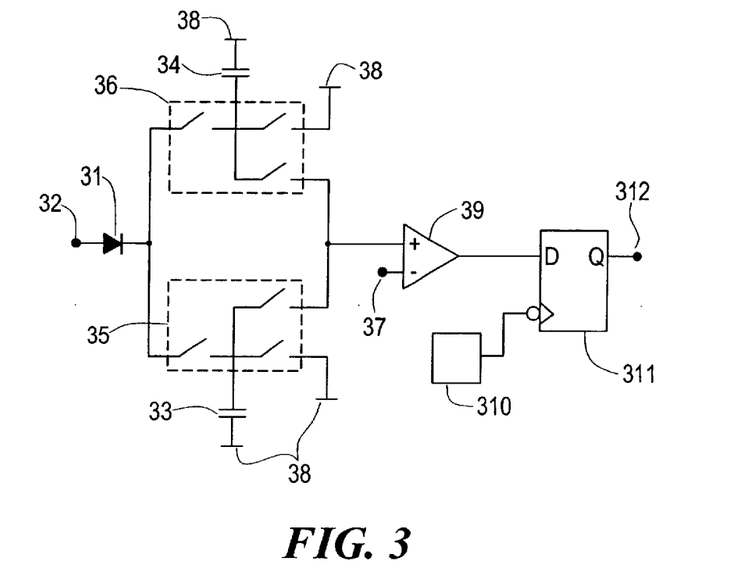
FIG. 3 schematically shows a circuit for envelope sampling
Figure 4:
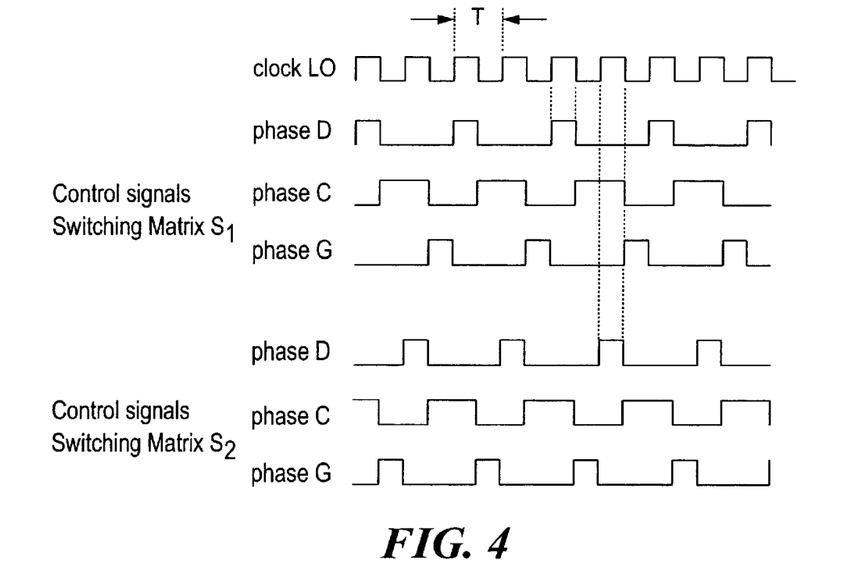
FIG. 4 shows control signals for envelope sampling

The envelope detection circuit proposed here, as shown in FIG. 3, comprises one rectifier diode 31, two sampling capacitors 33 and 34, a comparator 39, a flip flop 311, and a local oscillator (LO) 310 within the implant (FIG. 3). The LO-frequency $f_{LO}$ is assumed to be a multiple of the bit rate $f_{bit}$ (typically, $f_{LO}\approx 4f_{bit}$). The basic idea is to sample the envelope by means of two capacitors 33 and 34 and avoid the ohmic resistor 2 of above. By means of switching matrices 35 and 36, both sampling capacitors 33 and 34 are cyclically connected to one of three ports during Phases D, C, and G, respectively, as shown in FIG. 4:

Phase D: connection to the output of the rectifier diode 31 (input sampling),

Phase C: connection to one input of the comparator 39 (the other input is a reference dc-voltage 37 which is typically equal to about 50% of the rf-amplitude, as above), and Phase G: ground potential 38 (discharging).

The duration of phases D and G is T/2, respectively (T is one clock period of the LO). To minimize the power consumption of the comparator 39, the duration of phase C is T. The two sequences are offset by a phase shift of one T. At the end of phases C, the state of the comparator 39 output is clocked into a flip flop 311, i.e., the active slope is the negative slope of the LO-clock signal 310.

Employing a self clocking bit format, each of the capacitors 33 and 34 is charged and discharged about once in one bit period. Thus the power consumption involved with charging/discharging of the two capacitors 33 and 34 is $$P_{charge} = 2f_{bit}\frac{C_1U^2}{2} + 2f_{bit}\frac{C_2U^2}{2} = f_{bit}(C_1+C_2)U^2.$$

The exact size of the capacitors 33 and 34 is of minor importance, since it is not necessary to implement a particular time constant. Charging and discharging should be sufficiently fast, and influences of charge injection should remain within acceptable limits. Therefore, capacitors which are typically employed in switched capacitor designs, such as capacitors 33 and 34=1 pF, seem to be practical. Assuming such capacitors, a bit rate $f_{bit}$=600 kHz, and an rf-amplitude U=5V results in $P_{charge}$=0.03 mW. Supposing a LO-power consumption of typically $P_{LO}$=0.25 mW results in $P_{tot}=P_R+P_{LO}$=0.28 mW, which is significantly lower than the comparable power consumption for the standard envelope detection approach.

Synchronization Limits

In practical applications, the ratio between the incoming bit rate $f_{bit}$ and the LO rate $f_{LO}$ may not be exactly known. Nevertheless, correct bit synchronization should be guaranteed within defined limits. In one embodiment, the LO is completely free-running, and the synchronization is achieved fully digital. There is no frequency- or phase tracking adjustment, e.g., by means of frequency- or phase locked loops.

Employing a self clocking bit format as described above, the four different states L1, H1, L2, and H2 of the incoming data stream have to be distinguished. For the determination of theoretical synchronization limits, ideal system behavior is assumed. In particular, if one of the sampling capacitors 33 or 34 is connected to the rectifier diode 31 (Phase D), and the rf-carrier 32 applies only during a fraction of Phase D, then the capacitor is charged instantaneously and remains charged until discharging-Phase G. Only if no rf-carrier 32 appears during Phase D, the capacitor remains uncharged. Furthermore, it is supposed that the flip flop output 311 represents the charging state of the sampling capacitor, delayed by one LO clock period. The output results are Q=1, if the rf-carrier 32 was switched on during Phase D, and Q=0, if it remained switched off.

TABLE 1

Theoretical synchronization limits for input states L1, L2, H1, and H2

| Input state | Minimum duration | Maximum duration | Output code Q |
|---|---|---|---|
| L1 | 3T/2 | | 0 |
| | | 5T/2 | 00 |
| L2 | 7T/2 | | 000 |
| | | 9T/2 | 0000 |
| H1 | 3T/2 | | 11 |
| | | 5T/2 | 111 |
| H2 | 7T/2 | | 1111 |
| | | 9T/2 | 11111 |

An unambiguous association of input stages and bit patterns of the flip flop 311 output is summarized in Table 1. For example, a "short high", H1, is detected, if the output bit pattern (flip flop output Q) contains two or three ones. If the duration of H1 at the lower limit 3T/2, then the output bit pattern is Q=11, a duration at the upper limit 5T/2 results in pattern Q=111. Any duration between these limits yields two or three ones, dependent on the instantaneous phase shift between the LO clock signal 310 and the input 32. The code word with minimum length is Q=0 for an L1-state with duration 3T/2. The limits for minimum and maximum bit duration (assuming the self clocking bit format and a duty cycle of 50%) are imposed by the limits of the longest possible input states. For the self-clocking bit format, these states are the "long-" states L2 and H2. Correct bit decoding can take place for a bit duration B within the range $$\left[\frac{7}{2}T < B < \frac{9}{2}T\right],$$

or equivalently, for a bit rate $f_{bit}$ within the range $$\left[\frac{2}{9}f_{LO} < f_{bit} < \frac{2}{7}f_{LO}\right].$$

Assuming a fixed LO-rate of $f_{LO}$=2.4 MHz, the corresponding range for the bit rate is [533 bit/s<$f_{bit}$<685 kbit/s]. For a given bit rate of $f_{bit}$=600 kbit/s, the corresponding range for the LO rate is [2.1 MHz<$f_{LO}$<2.7 MHz].

Figure 5A:
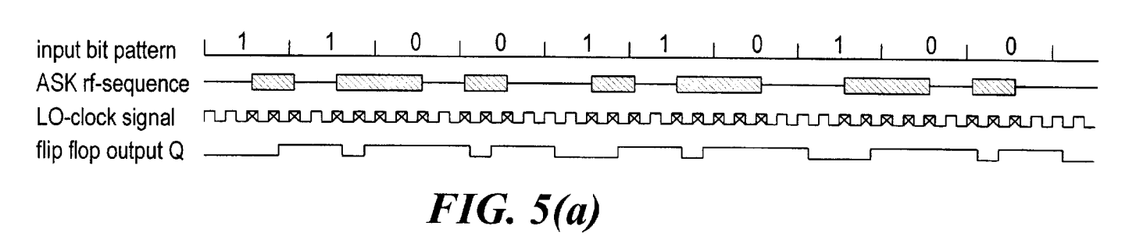
Figure 5B:
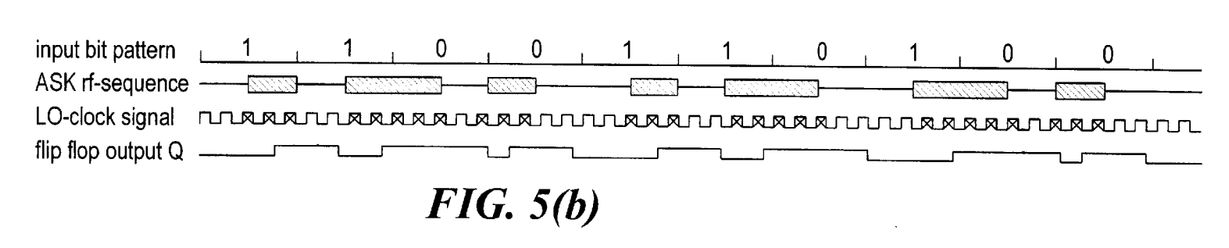
Figure 5C:
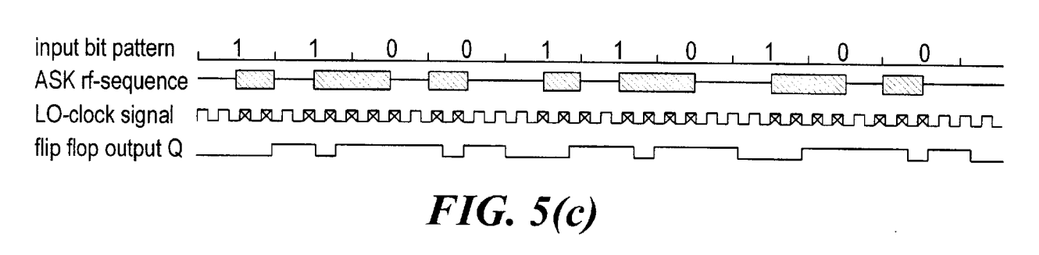

FIG. 5 depicts an example for correct bit decoding at different ratios between $f_{LO}$ and $f_{bit}$. The four traces in each of the subplots (a), (b), and (c) show an example of an input bit pattern, the associated ASK-sequence of the bits in self-clocking format, the LO-clock signal 310, and the output of the flip flop 311, respectively. The LO-clock rate is equal for all subplots. For clarity, the sampling phases where rf-amplitude are present during phase D are marked with a cross. The flip flop output 311 signal exactly follows the patterns of the cross-phases, delayed by one LO-clock period. In subplot (a) the ratio is exactly $$f_{bit} = \frac{f_{LO}}{4.0}$$

(nominal ratio), but a phase shift between the LO-clock signal and the ASK-sequence is introduced. In the example shown, states H1, L1, H2, and L2 are detected as flip-flop output patterns 111, 0, 11111, and 000, respectively (cf. Table 1). In subplots (b) and (c), the bit rates at the upper and at the lower limits, i.e., $$f_{bit} \approx \frac{f_{LO}}{3.6} \text{ and } f_{bit} \approx \frac{f_{LO}}{4.4},$$

respectively. As demonstrated, the output code allows an unambiguous detection of the four possible input states corresponding to Table 1, and therefore correct bit decoding is possible. In a practical application, the actual bit decoding is done by means of subsequent logic circuitry (not shown here).

Special Bit Formats ("Triplet-sequences")

Figure 6:
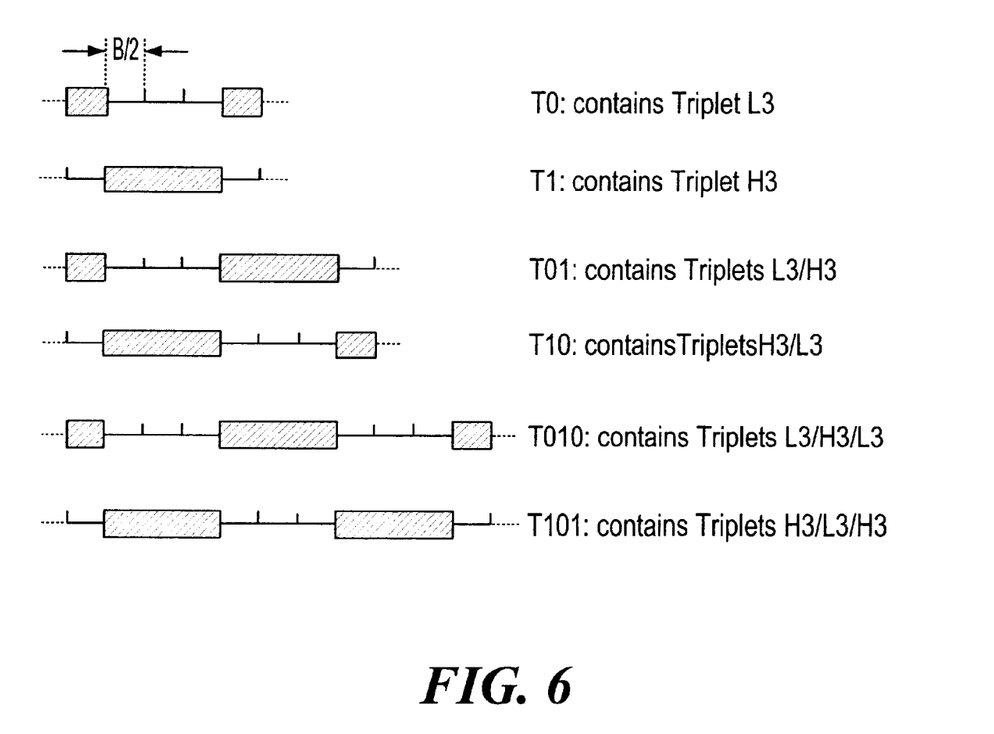
FIG. 6 shows examples of triplet sequences

Some embodiments use so called "triplet-sequences", as shown in FIG. 6. A triplet sequence contains states where the RF-carrier is switched on (or off) for a duration of 3B/2, resulting in states L3 and H3, respectively. These states can unambiguously be distinguished from states L1, H1, L2, and H2.

Triplet sequences in general are composed of
 a. a starting short state L1 or H1;
 b. a sequence of strictly alternating states L3 and H3;
 c. terminating short state L1 or H1.

The starting and terminating short state are complementary to the neighboring states L3 or H3. Triplet sequences are abbreviated, e.g., as T010, and T010 consists of states H1 L3 H3 L3 H1. These conditions allow triplet sequences to be unambiguously detected when they are embedded into bits with self-clocking format.

Each triplet sequence is associated with a particular parity: triplet sequences starting with H1, i.e., T0, T01, T010, etc., have even parity, triplet sequences starting L1, i.e., T1, T10, T101, etc., have odd parity.

The decoding of triplets L3 and H3 does not require additional analog hardware as compared to the decoding of states L1, H1, L2, and H2 only. However, an unambiguous detection of L3 and H3 results in a slight reduction of synchronization limits. Duration limits for L3 and H3 are summarized in Table 2 (which can be regarded as extension of Table 1).

TABLE 2

Theoretical synchronization limits for states L3 and H3

| Input state | Minimum duration | Maximum duration | Output code Q |
|---|---|---|---|
| L3 | 11T/2 | | 00000 |
| | | 13T/2 | 000000 |
| H3 | 11T/2 | | 111111 |
| | | 13T/2 | 1111111 |

Correct bit- and triplet decoding (assuming the self clocking bit format with a duty cycle of 50%) requires a bit duration B within the range $$\left[\frac{11}{3}T < B < \frac{13}{3}T\right],$$

or equivalently, a bit rate $f_{bit}$ within the range $$\left[\frac{3}{13}f_{LO} < f_{bit} < \frac{3}{11}f_{LO}\right].$$

Assuming a fixed LO-rate of $f_{LO}$=2.4 MHz, the corresponding range for the bit rate is [554 bit/s<$f_{bit}$<655 kbit/s], and for a given bit rate of $f_{bit}$=600 kbit/s, the corresponding range for the LO rate is [2.2 MHz<$f_{LO}$<2.6 MHz].

Data Word Format for Active Stimulation Modes Based on Triplet Sequences

Triplet sequences can very effectively be used in data transfer protocols. In the cochlear implant described herein, the transcutaneous transfer of stimulation information is achieved by means of data words, the bit rate is $f_{bit}$=600 kbit/s. Each data word is composed of a starting triplet sequence, a particular number of information bits (with self-clocking format), and a terminating triplet sequence.

The overall information can be divided into "static-" and "dynamic" information. Static information comprises e.g., information concerning phase durations or reference current levels. One "static information vector" comprises 64 bits. The transfer to the implant is achieved by means of one particular bit within each data word. Static information is transmitted continuously and stored in a memory within the implant. Dynamic information comprises instantaneous electrode addresses and stimulation amplitudes.

The data word format as described herein allows high rate stimulation strategies based on sign-correlated, simultaneous stimulation pulses. Sign-correlated means that the pulses are 100% overlapping in time and that for each phase, the signs of current flow are identical.

The following active stimulation modes are possible:
a. stimulation with sign-correlated biphasic, symmetrical pulses;
b. stimulation with sign-correlated triphasic, symmetrical pulses; and
c. stimulation with sign-correlated triphasic pulses (precision mode).

Biphasic Stimulation Mode

In the biphasic mode, stimulation is achieved by means of symmetrical, charge balanced current pulses, with equal durations of the two phases.

Data words in the biphasic stimulation mode are composed as follows:

T01(or T10) ST SIGN EL_AMP$_1$ (optional: EL_AMP$_2$ . . . ) T0 (or T1)

The starting triplet sequence is either T01 or T10. The first following bit ST carries the static information. If bit ST is the first bit of the 64-bit static information vector, the starting sequence is T01, otherwise it is T10. Bit SIGN defines the sign of the first phase of the biphasic pulses: BIT='0' means cathodic first, BIT='1' means anodic first. Blocks EL_AMP$_i$ are composed of 11 bits, respectively. Each block contains four address bits (EL4 . . . EL1) and seven amplitude bits (AMP7 . . . AMP1):

EL4 . . . EL1 AMP7 . . . AMP1

The number of blocks EL_AMP$_i$ defines the number of simultaneous channels. E.g., five blocks EL_AMP$_i$ with different addresses elicit five simultaneous sign-correlated pulses.

Each data word is terminated by either sequence T0, or T1, depending on the to parity of preceding bits of the data word. The terminating sequence is selected to obtain odd parity of the overall data word.

With the durations 4 B and 2.5 B for the starting sequence T01 (or T10) and the terminating sequence T0 (or T1), respectively, and the number N of simultaneous channels, the maximum stimulation rate $R_2$ for stimulation with biphasic pulses is $$R_2 = \frac{600}{8.5 + 11N} \text{ kpulses/sec.} \qquad (1)$$

Triphasic Stimulation Mode

In the triphasic mode, stimulation is achieved by means of charge balanced triphasic current pulses, with equal durations of the three phases. The signs and amplitudes of the first and third phases are equal, and for the second phase, the sign is opposite, and the amplitude is twice. In the following, such pulses are designated as "triphasic symmetrical pulses".

Data words in the triphasic stimulation mode are similar to those of the biphasic mode:

T010(or T101) ST SIGN EL_AMP$_1$ (optional: EL_AMP$_2$ . . . ) T0(or T1)

The starting triplet sequence is either T010 or T101. The first following bit ST carries the static information. If bit ST is the first bit of the 64-bit static information vector, the starting sequence is T010, otherwise it is T101. Bit SIGN defines the sign of the first phase of the triphasic pulses: BIT='0' means cathodic first, BIT='1' means anodic first. Blocks EL_AMP$_i$ are composed of 11 bits, respectively. Each block contains four address bits (EL4 . . . EL1) and seven amplitude bits (AMP7 . . . AMP1):

EL4 . . . EL1 AMP7 . . . AMP1

The number of blocks EL_AMP$_i$ defines the number of simultaneous channels. E.g., five blocks EL_AMP$_i$ with different addresses elicit five simultaneous sign-correlated pulses.

Each data word is terminated by either sequence T0, or T1, depending on the parity of preceding bits of the data word. The terminating sequence is selected to obtain odd parity of the overall data word.

With the durations 5.5 B and 2.5 B for the starting sequence T010 (or T101) and the terminating sequence T0 (or T1), respectively, and the number N of simultaneous channels, the maximum stimulation rate $R_3$ for stimulation with triphasic pulses is $$R_3 = \frac{600}{10 + 11N} \text{ kpulses/sec.} \qquad (2)$$

Triphasic Stimulation—Precision Mode

In the triphasic precision mode, stimulation is achieved by means of charge balanced triphasic current pulses, with equal durations of the three phases. Here, the amplitudes of the first and second phases can be defined, and the third amplitude is the computed as the difference between the second and the first amplitude (zero net charge).

Data words in the triphasic precision mode are composed as follows:

T01010 (or T10101) . . .
ST SIGN EL_AMP_AMP$_1$ (optional: EL_AMP_AMP$_2$ . . . ) T0 (or T1)

The starting triplet sequence is either T01010, or T10101. The first following bit ST carries the static information. If bit ST is the first bit of the 64-bit static information vector, the starting sequence is T01010, otherwise it is T10101. Bit SIGN defines the sign of the first phase of the triphasic pulses: BIT='0' means cathodic first, BIT='1' means anodic first. Blocks EL_AMP_AMP$_i$ are composed of 18 bits, respectively. Each block contains four address bits (EL4 . . . EL1) and seven amplitude bits (AMP_A7 . . . AMP_A1) for the first phase, and seven amplitude bits (AMP_B7 . . . AMP_B1) for the second phase:

EL4 . . . EL1 AMP_A7 . . . AMP_A1 AMP_B7 . . . AMP_B1

The number of blocks EL_AMP$_i$ defines the number of simultaneous channels. E.g., five blocks EL_AMP$_i$ with different addresses elicit five simultaneous sign-correlated pulses.

Each data word is terminated by either sequence T0, or T1, depending on the parity of preceding bits of the data word. The terminating sequence is selected to obtain odd parity of the overall data word.

With the durations 8.5 B and 2.5 B for the starting sequence T01010 (or T10101) and the terminating sequence T0 (or T1), respectively, and the number N of simultaneous channels, the maximum stimulation $R_{3,precision}$ for stimulation with triphasic pulses in the precision mode is $$R_{3,precision} = \frac{600}{13 + 18N} \text{ kpulses/sec.} \qquad (3)$$

In Table 3 the maximum stimulation rates according to Eqs. (1), (2), and (3) are computed as a function of the number N of simultaneous channels.

TABLE 3

Maximum stimulation rates for biphasic and triphasic pulses

| N | $R_2$ (kpulses/sec) | $R_3$ (kpulses/sec) | $R_{3,precision}$ (kpulses/sec) |
|---|---|---|---|
| 1 | 30.77 | 28.57 | 19.35 |
| 2 | 19.67 | 18.75 | 12.24 |
| 3 | 14.46 | 13.95 | 8.96 |
| 4 | 11.43 | 11.11 | 7.06 |
| 5 | 9.45 | 9.23 | 5.83 |
| 6 | 8.05 | 7.89 | 4.96 |
| 7 | 7.02 | 6.90 | 4.31 |
| 8 | 6.22 | 6.12 | 3.82 |
| 9 | 5.58 | 5.50 | 3.43 |
| 10 | 5.06 | 5.00 | 3.11 |
| 11 | 4.63 | 4.58 | 2.84 |
| 12 | 4.27 | 4.23 | 2.62 |

Figure 7A:
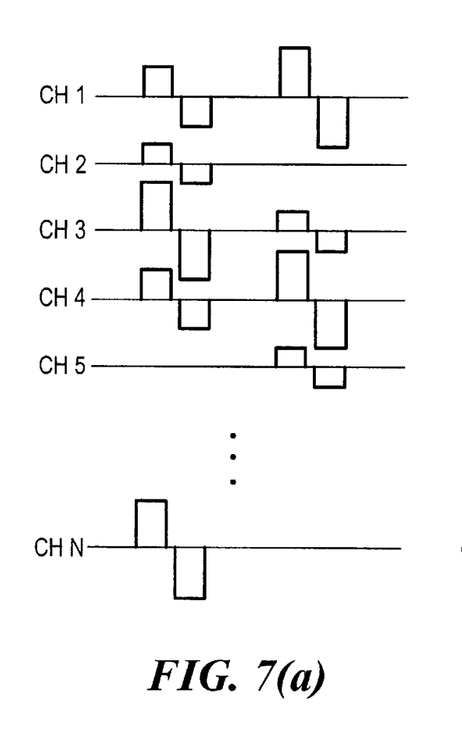
Figure 7B:
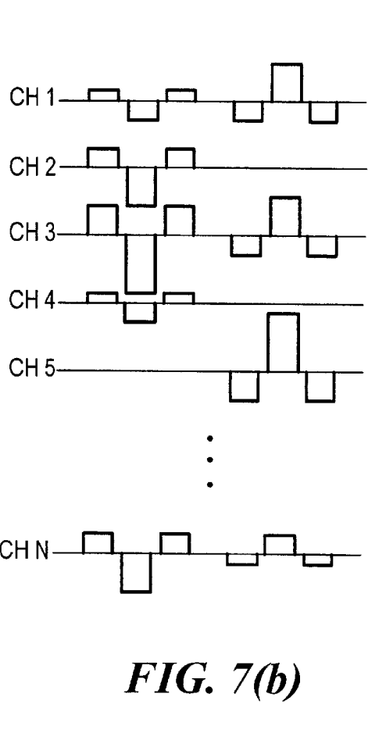
Figure 7C:
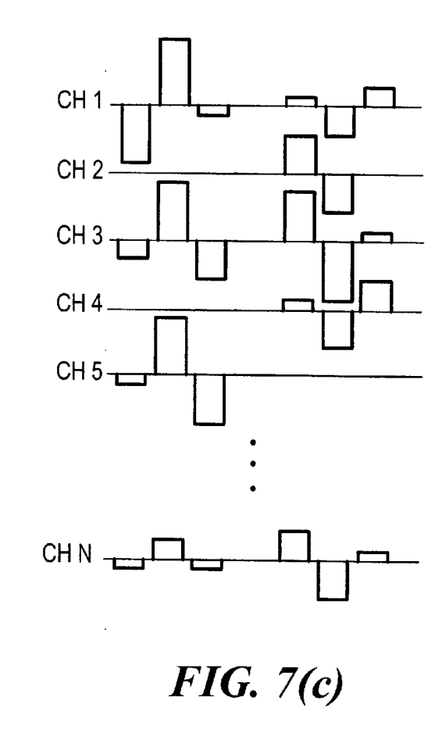

Examples of pulse shapes of possible stimulation modes are shown in FIG. 7.

Format of Static Information Vector

The format of the 64-bit static information vector is shown in Table 4.

TABLE 4

Format of static information vector

| Data word # | Bit ST | Description |
|---|---|---|
| 1 | 1D16 | Identification (16 Bit) |
| 2 | 1D15 | |
| . | . | |
| . | . | |
| . | . | |
| 16 | ID1 | |
| 17 | REF2 | Reference current range (channel 1) (2 Bit) |
| 18 | REF1 | |
| 19 | REF2 | Reference current range (channel 2) (2 Bit) |
| 20 | REF1 | |
| . | . | |
| . | . | |
| . | . | |
| 47 | REF2 | Reference current range (channel 16) (2 Bit) |
| 48 | REF1 | |
| 49 | DUR8 | Pulse duration (8 Bit) |
| . | . | |
| . | . | |
| 56 | DUR1 | |
| 57 | CRC8 | CRC check (8 Bit) |
| . | . | |
| . | . | |
| . | . | |
| 64 | CRC1 | |

Each individual implant is associated with a characteristic 16-bit identification sequence, which is stored to a permanent implant memory during production. Active stimulation is possible, if the 16 bits ID16 . . . ID1 of the static information vector coincide with the implant specific identification sequence (however, the system can also be activated by a general, non-implant-specific 16 bit identification sequence). Bits REF2 REF1 define the reference current range for each stimulation channel. Bits DUR8 . . . DUR1 defined the duration of the phases of biphasic and triphasic pulses. Bits CRC8 . . . CRC1 are used to implement a Cyclic-Redundancy-Check for save data transfer.

Modification of Phase Duration

As stated above, the phase duration is defined by an 8-bit word in the static information vector. The default setting is that the phase duration is equal for all pulses and all channels. However, in some cases it might be useful to vary the phase duration of single or sign-correlated stimulation pulses. In the cochlear implant described the phase duration can be enhanced by adding a sequence of logical "ones" to the terminating triple sequence T0 (or T1) of a data word. Each logical "one" enhances the phase duration by exactly 25% of its default value defined by bits DUR8 . . . DUR1 in the static information vector. The sequence of logical "ones" is terminated by either a logical "zero" or a triplet sequence. Examples:

(1) . . . 0 1 T0 T10 0 0 1 . . .
(2) . . . 0 0 T1 0 1 0 1 1 T10 1 0 1 . . .
(3) . . . 0 1 T1 1 0 T0100 1 . . .
(4) . . . 1 0 T0 1 1 1 0 1 0 T01 . . .

In pattern (1) the terminating sequence T0 of the data word is immediately followed by starting pattern T10 (biphasic pulse), and therefore the phase duration of pulse starting immediately after T0 is equal to the value defined by bits DUR8 . . . DUR1 in the static information vector.

In pattern (2) the terminating pattern T1 is followed by a logical "zero", and therefore the phase duration of elicited pulse again is equal to the value defined by bits DUR8 . . . DUR1 in the static information vector.

In pattern (3) the terminating pattern T1 is followed by a logical "one", and therefore the phase duration of elicited pulse is enhanced by 25% of the value defined by bits DUR8 . . . DUR1 in the static information vector. In patterns (4) the terminating pattern T0 is followed by a sequence of three logical "ones", therefore the phase duration of elicited pulse is enhanced by 75% of the value defined by bits DUR8 . . . DUR1 in the static information vector.

Note that for sign-correlated pulses the enhancement of the phase duration applies for all simultaneously activated stimulation pulses.

Generation of Sign-correlated Simultaneous Pulsatile Stimuli

As stated above, the cochlear implant presented here allows to generate sign-correlated pulsatile stimuli in two or more simultaneously activated electrode channels, as shown in FIG. 7. The pulse waveforms are equal in time and sign (i.e., the directions of the current flows), and the reference electrode is a remote ground electrode (monopolar stimulation). However, it should be noted that it is not required that the pulse waveforms be equal in time.

Employing sign-correlated stimuli ensures that the sum of all currents delivered by the individual current sources is always forced to flow into the reference electrode. Thus the quantity of depolarizing (negative) charge delivered to the excitable nervous tissue is well defined. This permits—at least to a certain extent with regard to spatial channel interaction—to generate more subtly differentiated and more sophisticated activation profiles as compared to the current standard CIS-strategy, where only one profile is associated with each channel.

If sign-correlation is not ensured, the conducting tissue within the scala tympani may act as a shunt resistor between active electrodes. For example, if two neighboring electrodes sink and source a particular current simultaneously, most of the current will flow within the scala tympani from one electrode into the other, and it does not reaches the intended site of excitable nervous tissue.

Figure 8:
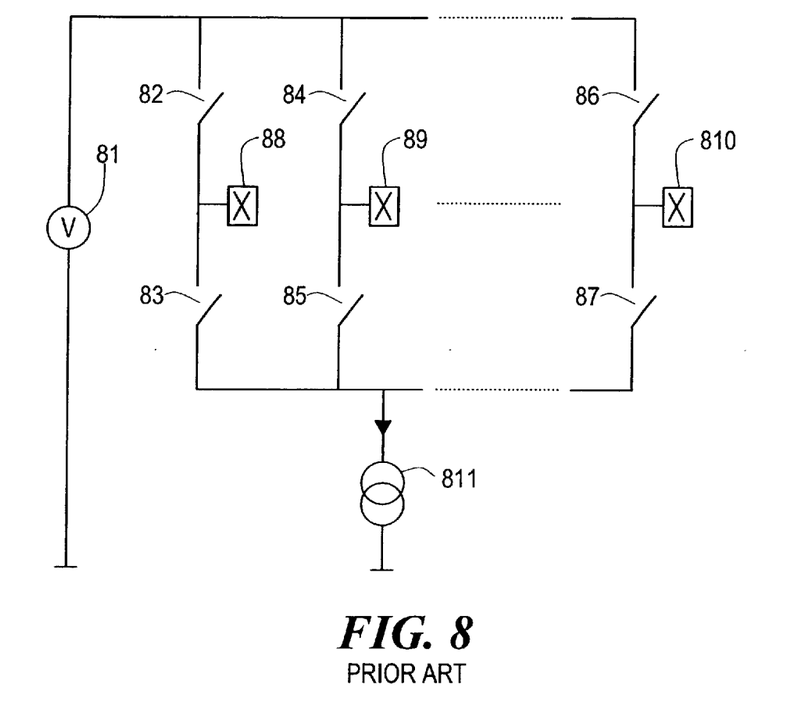

The generation of non-overlapping pulses can be achieved, e.g., as depicted in FIG. 8 (prior art). If a particular channel is active, the corresponding electrode $E_i$ 88 or 89 and the remote ground electrode RG 810 are connected to the supply voltage rail $V_{DD}$ 81 and the input of the stimulation current source 811, respectively, for the first phase of the pulse, and vice versa for the second. The advantage of such a configuration is that the minimum supply voltage of the implant is only $V_{DD,min} \approx V_{stim,max}$, where $V_{stim,max}$ is the maximum expected voltage drop during one phase between the stimulation electrodes (assuming an ideal current source).

Such a switching concept is not practical in general, if two or more independent current sources are activated simultaneously. This requires that the remote ground has to be connected to a fixed potential, e.g., to $V_{DD}/2$, resulting in a minimum implant supply voltage of $V_{DD,min} \approx 2*V_{stim,max}$. This is twice the minimum supply voltage of above and results in a significantly enhanced implant power consumption.

Figure 9:
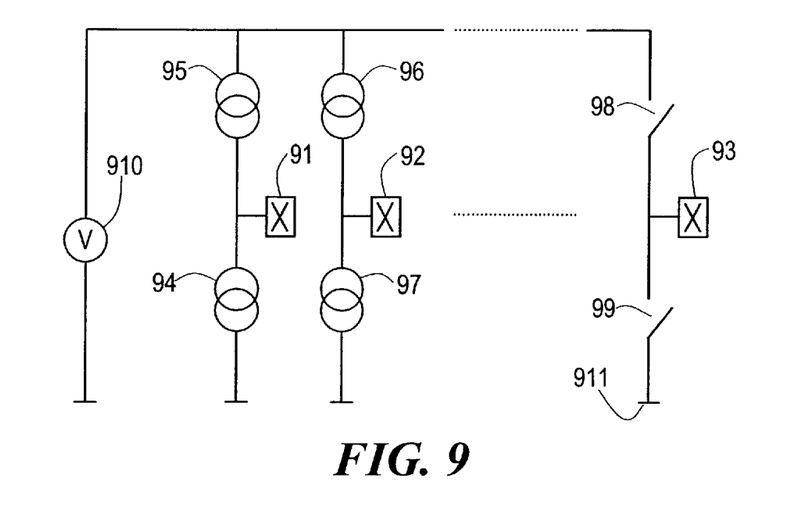
FIG. 9 schematically shows a circuit for generation of sign-correlated simultaneous stimulation pulses FIG. 10 EAP generation and measurement    a. schematically shows a circuit    b. schematically shows an equivalent electrical circuit

However, the advantage of having only $V_{DD,min} \approx V_{stim,max}$ and at the same time to allow for simultaneous stimulation of two or more channels can be maintained, if the signs and temporal waveforms of simultaneous pulses are assumed to be equal. This allows for a concept as shown in FIG. 9. Here each stimulation electrode $E_i$ 91 or 92 is connected to two current sources 94 and 95 or 96 and 97, one for each sign, and the common remote ground electrode 93 is switched to either $V_{DD}$ 910 or ground potential GND 911. For stimulation, either all upper or all lower current sources are activated simultaneously, and thus the current forced to flow into electrode RG 93 is equal to the sum of absolute values of all single electrode currents.

EAP-measurement System

Figure 10A:
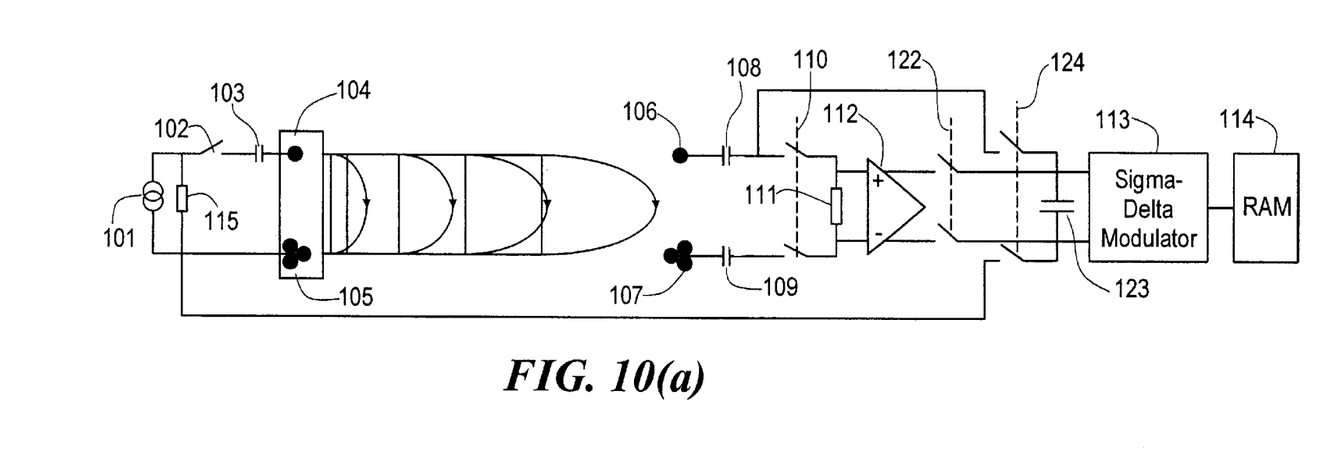
Figure 10B:
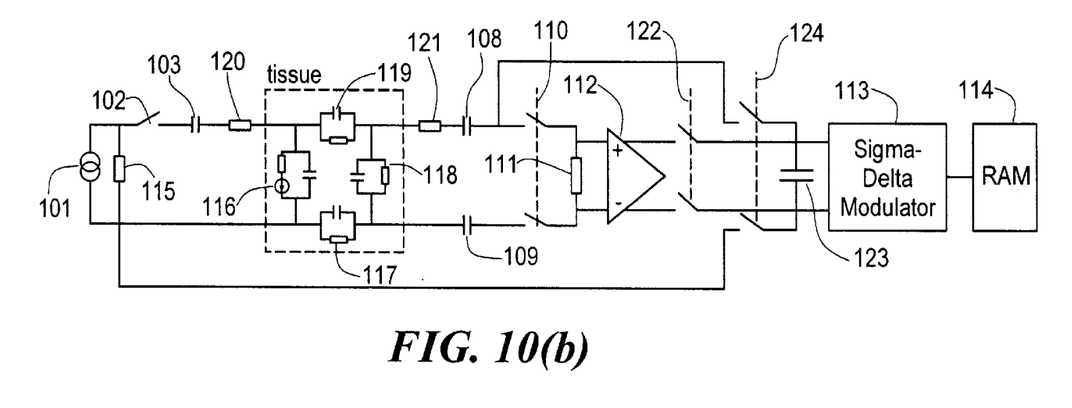

The situation of electrical stimulation and detection of the EAPs is depicted in the simple model FIG. 10(a) and in the electrical equivalent circuit FIG. 10(b).

The system for stimulation in FIG. 10(a) consists of the stimulation current source $I_{STIM}(t)$ 101 (output resistor 115), switch 102, the (discrete) coupling capacitor 103 and the stimulation electrode pair, i.e., an intracochlear stimulation electrode 104 and a (remote) reference electrode 105. The system for measurement also consists of an electrode pair, i.e., a measurement electrode 106 (which is different from the stimulation electrode 104), and a (remote) reference electrode 107 (also different from the stimulation reference electrode 105), double switches 110, 122, and 124, sampling capacitor 123, double the (discrete) coupling capacitors 108 and 109, a differential amplifier 112 (instrumentation amplifier), a sigma-delta modulator 112, and a memory 114 (RAM).

In the equivalent circuit FIG. 10(b) the intracochlear electrodes are replaced by nonlinear, frequency dependent interface impedances $Z_S(\omega)$ 120, and $Z_M(\omega)$ 121, respectively, as described by Mayer S., Geddes L. A., Bourland J. D., Ogborn L., "Faradic resistance of the electrode/electrolyte interface," Med. & Biol. Eng.& Comput. (30):538–542 (1992); Ragheb T., Geddes L. A., "Electrical properties of metallic electrodes," Med. & Biol. Eng.& Comput. (28):182–186 (1990), which is incorporated herein by reference. In a rough approximation, the tissue is replaced by a network composed of discrete RC two-ports 116–119, with $R_iC_i = \in_0 \in_r/\gamma$ (i=1, 2, 3, and 4), and specific conductivity $\gamma$ and relative dielectric constant $\in_r$. One of the two-ports 116 contains voltage source $U_{EAP}(t)$, representing the generated EAP. The impedances of the two reference electrodes are neglected here.

Stimulation

For stimulation, a charge balanced pulse of a particular duration is delivered from the current source across the closed switch 102 and capacitor 103 into the tissue. With the cochlear implant described herein, symmetrical biphasic, symmetrical triphasic, and pulses in the triphasic precision mode can be applied. The stimulus charges all capacitors of the system FIG. 10(b), i.e., the capacitances within the interface impedances, as well as the distributed capacitances of the tissue. The (passive) voltage response of the tissue to the stimulus is designated as "artifact". Artifact amplitudes at the input of the amplifier typically are in between 100–200 mV, i.e., 2 to 3 orders of magnitude higher than the expected EAP-amplitudes. After the current impulse is finished, switch 102 is switched off. This ensures that no further current can flow across the interface impedance $Z_S(\omega)$ 120, and hence relaxation procedures within the electrode interfaces are decoupled from relaxation procedures of the tissue. In order to avoid an overload condition of the instrumentation amplifier, double switch 110 is switched off during the stimulus applies.

Generation of EAPs

The stimulation pulse causes action potentials in a particular number of neurons. If an action potential occurs, the changes from the equilibrium potential difference at the membrane of the axon between inside and outside typically are about 100 mV, as described by Frijns J., ten Kate J., "A model of myelinated nerve fibres for electrical prosthesis design," Med. & Biol. Eng. & Comput. 32(4):391–398 (1994), which is incorporated herein by reference. However, the absolute potential change at the outside typically is less than 1 mV, as described by Rattay F., "Analysis of models for external stimulation of axons," IEEE-Trans. Biomed. Eng. vol. 33, No.10:974–977 (October 1986), which is incorporated herein by reference. The superposition of absolute potential differences at the outsides of many firing neurons results in the EAP (also sometimes designated as "whole nerve action potential" or "compound action potential"). The nerves are firing with a particular delay referred to the stimulating pulse (latency), and in general the EAP appears after the stimulation pulse has finished. However, when the EAP occurs, the relaxation of the tissue usually is not finished. This means that at the input of the amplifier—after the stimulus current impulse—there is a fraction of voltage $U_{EAP}(t)$, superposed by an exponentially decreasing voltage due to the passive relaxation of the tissue. This voltage after the current stimulus is designated in the following as "residual artifact". The size of the residual artifact depends on the shape of the preceding stimulation pulse. Theoretically, triphasic pulses cause less residual artifact than biphasic pulses. If two of the three phases of a triphasic pulse can be set individually—as can be done in the described cochlear implant in the triphasic-precision mode—the residual artifact can be reduced to a minimum.

Measurement of EAPs

If the EAP-measurement mode is initiated (see below), double switches 110 and 122 are switched on (low impedance) for a duration of 1.7 ms (measurement window), and double switch 124 remains open (high impedance). In this switch configuration, the input signal 106 is amplified in the instrumentation amplifier 112 by a factor of 100 (fixed gain), and subsequently inputted to the sigma-delta modulator 113. The sigma-delta modulator 113 ($1^{st}$ order) is operated as an additional amplifier with programmable gain (possible gains: 5, 10, 20, and 40), and converts the analog signal into a high-frequency 1-bit sequence at a rate of 1.2 MHz. The sigma-delta modulator can also be configured as an adaptive modulator with gain 5, as described by Zierhofer C. M., "Adaptive Sigma-Delta Modulation with one bit quantization," IEEE-Trans. CAS II, vol. 47, No.5:408–415 (May 2000), which is incorporated herein by reference. The sigma-delta-sequence is directly clocked into a 2048×1-bit RAM 114.

Once invoked, the measurement procedure works autonomously, and no further instructions from outside are necessary. To avoid possible disturbances during measurement due to data sequences in the rf-link, usually a continuous-wave rf-carrier is applied.

Optionally, double switch 122 can be controlled by triplet sequence T1010, which is designated as "hold-mode interrupt". If T1010 does not appear during the measurement window, double switch 122 remains in the on-state. If T1010 appears for the first time within the measurement window, double switch 122 is opened (hold-mode). The signal value which applies immediately before switch-opening is stored in sampling capacitor 123 and applies as a constant value at the input of the sigma-delta modulator 113. If T1010 is applied during the hold-mode, double switch 122 is closed for about 2 µs and thus the signal at the output of amplifier 112 is sampled and stored in sampling capacitor 123.

The hold-mode option allows a more accurate analysis of the EAP signal at one or more selected time instants within the measurement window. If the EAP-signal applies repetitively, an improved analysis accuracy of the overall EAP-signal can be obtained by proper selection of analysis time instants.

Although hold-mode sequence T1010 interrupts the continuous-wave rf-carrier applying in the measurement window, the disturbing influence should be negligible due to its short duration of only about 12 µs.

Artifact Measurement System

The sigma-delta modulator 113 can also be used to measure the size of stimulus artifacts. In contrast to EAP-measurement, this system requires that a stimulation pulse applies. After initialization of the artifact measurement system (see below), double switches 110 and 122 are open, and double switch 124 is closed. Thus an addressed measurement electrode 106 (after output capacitor 108) and the stimulation reference ground electrode 105 is connected to sampling capacitor 123. At the end of the stimulation pulse, or at a time instant controlled by the hold-mode interrupt T1010 (cf. EAP-measurement system), the sampling capacitor is connected to sigma-delta-modulator 113. The voltage analyzed by the sigma-delta modulator to 113 is a constant voltage. The sigma-delta data sequence is clocked into the RAM 114.

If the measurement electrode is equal to the stimulation electrode address, the artifact allows to estimate the electrode impedance. If the measurement electrode is different from the stimulation electrode, the artifact represents the voltage response to the stimulation pulse at this particular electrode position. By addressing a number of electrodes, the voltage distribution within the scala tympani as response to a stimulation pulse can be estimated.

Initialization of EAP—and Artifact Measurement Modes

The measurement mode of the cochlear implant described herein in general is invoked with the following data word:

T0101 MM8 . . . MM1 T0 (or T1)

Starting triplet sequence T0101 is followed by eight bits MM8 . . . MM1, which define the settings of the measurement mode (e.g., EAP—or artifact measurement mode, measurement electrode address, sigma-delta modulator configuration, etc.). The terminating sequence is either sequence T0, or T1, selected to obtain odd parity of the overall data word.

Read-back Modes

The transfer of information from the implant to outside in general is achieved by means of load modulation. For load modulation, the quality factor of the rf-receiver circuit within the implant is reduced, and this reduction is detected outside. In the present application, digital data are transmitted by means of load modulation at a rate of 300 kbits/sec.

Both the contents of the RAM 114, and the 64-bit static information vector can be read back. Optionally, a self clocking bit format for read-back can be selected. The duration of the read-back of the 2048×1-RAM at 300 kbit/sec is about 7 ms. Thus, together with the duration of 1.7 ms for the measurement window, the maximum repetition rate for EAP-measurements is more than about 100 Hz.

The read-back of the digital data stored in implant-memories is initiated by particular triplet sequences (so-called interrupts). Four different interrupts are defined (Table 5).

TABLE 5

Summary of read-back interrupts

| Logical | Overall duration | Function |
|---------|------------------|----------|
| T010101 | 16.666 µs (= 10B) | Start read-back RAM (simple bit format) |
| T101010 | 16.666 µs (= 10B) | Start read-back static information vector (simple bit format) |
| T0101010 | 19.166 µs (= 11.5B) | Start read-back RAM (self clocking bit format) |
| T1010101 | 19.166 µs (= 11.5B) | Start read-back static information vector (self clocking) |

The processing of the 1-bit sigma-delta sequence can comfortably be accomplished off-line, and a lot of computational power can be used for improved reconstruction of the EAP-waveforms. For example, non-linear decoding techniques can be applied for enhanced signal-to-noise ratio, as described by Thao N. T. and Vetterli M., "Deterministic analysis of oversampled A/D conversion and decoding improvement based on consistent estimates," IEEE-Trans. Signal Proc., vol. 42, No. 3.:519–531 (March 1994), which is incorporated herein by reference.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A circuit for generating a sign-correlated simultaneous pulsatile stimulation comprising:
   a. a plurality of circuit paths coupled in parallel between a voltage rail and ground, each circuit path comprising an electrode coupled to the voltage rail via a first current source and to the ground via a second current source, the first current source and the second current source having opposite sign;
   b. a remote ground electrode coupled to the voltage rail via a first switch, the remote ground electrode further coupled to ground via a second switch;
   wherein the stimulation is achieved by activating all current sources of the same sign and switching the remote ground electrode to create a current in the remote ground electrode equal to the sum of all single electrode currents.

2. A circuit according to claim 1, that generates the sign-correlated simultaneous pulsatile stimulation in a cochlear implant.

3. A circuit according to claim 1 that can generate sign-correlated stimulation pulses applied substantially simultaneously on two or more circuit paths, the sign-correlated stimulation pulses selected from the group consisting of:
   a. sign-correlated biphasic, symmetrical pulses;
   b. sign-correlated triphasic, symmetrical pulses;
   c. and sign-correlated triphasic pulses.

4. A method of generating sign-correlated simultaneous pulsatile stimuli comprising:
   a. simultaneously applying current of same sign to a plurality of electrodes $E_i$; and
   b. switching a remote ground electrode directly to one of a voltage rail and a ground so as to create a current in the remote ground electrode equal to the sum of absolute values of all single electrode $E_i$ currents.

5. A method according to claim 4 wherein simultaneously applying current of same sign to a plurality of electrodes $E_i$, each electrode is coupled via a switch to either a first or second current source, the second current source having the opposite sign as the first current source.

6. A method according to claim 4, wherein the acoustic nerve is stimulated by the sign-correlated simultaneous pulsatile stimuli.

7. A method according to claim 4, that generates sign-correlated simultaneous pulsatile stimuli in a cochlear implant.

8. A method according to claim 4, wherein creating the current in the remote ground electrode includes creating pulses chosen from the group consisting of:
   a. sign-correlated biphasic, symmetrical pulses;
   b. sign-correlated triphasic, symmetrical pulses; and
   c. sign-correlated triphasic pulses.

* * * * *